(12) United States Patent
Caprotti et al.

(10) Patent No.: US 6,258,135 B1
(45) Date of Patent: Jul. 10, 2001

(54) LUBRICITY ADDITIVES FOR FUEL OIL COMPOSITIONS

(75) Inventors: Rinaldo Caprotti; Christophe Le Deore, both of Oxford (GB)

(73) Assignee: Exxon Chemical Patents Inc, Linden, NJ (US)

( * ) Notice: Subject to any disclaimer, the term of this patent is extended or adjusted under 35 U.S.C. 154(b) by 0 days.

(21) Appl. No.: 09/284,226

(22) PCT Filed: Sep. 15, 1997

(86) PCT No.: PCT/EP97/05105

§ 371 Date: Jul. 15, 1999

§ 102(e) Date: Jul. 15, 1999

(87) PCT Pub. No.: WO98/16596

PCT Pub. Date: Apr. 23, 1998

(30) Foreign Application Priority Data

Oct. 11, 1996 (GB) .................................................. 9621262

(51) Int. Cl.[7] .................................... C10L 1/18; C10L 1/22
(52) U.S. Cl. .................................... 44/389; 44/391; 44/400
(58) Field of Search ............................. 44/391, 400, 389

(56) References Cited

U.S. PATENT DOCUMENTS

| 3,273,981 | 9/1966 | Furey . | |
|---|---|---|---|
| 3,287,273 | 11/1966 | Furey et al. . | |
| 3,944,594 | 3/1976 | Kleiner et al. . | |
| 4,090,971 | 5/1978 | Hoke . | |
| 4,098,708 | 7/1978 | Stuebe . | |
| 4,444,567 | * 4/1984 | Burns et al. ........................... | 44/400 |
| 4,551,152 | 11/1985 | Sung . | |
| 5,089,158 | 2/1992 | Van Kruchten et al. . | |
| 5,427,591 | * 6/1995 | Cherpeck ............................... | 44/400 |
| 5,462,567 | 10/1995 | Cherpeck . | |
| 5,522,906 | 6/1996 | Hashimoto et al. . | |
| 5,734,078 | * 3/1998 | Feilden et al. ........................ | 562/477 |
| 5,792,339 | * 8/1998 | Russell .................................. | 44/300 |

FOREIGN PATENT DOCUMENTS

| 0771782 | * 5/1997 | (EP) . |
| 1505302 | 3/1978 | (GB) . |
| WO 94/14926 | 7/1994 | (WO) . |
| WO 94/17160 | 8/1994 | (WO) . |
| WO 95/11955 | 5/1995 | (WO) . |
| WO 9/17484 | 6/1995 | (WO) . |

OTHER PUBLICATIONS

Tyman, "Long–Chain Phenols. XII. Compositional Studies: The Polymeric Material in the Unsaturated Phenols of Anacardium Occidentale" (Abstract), 1978.*

* cited by examiner

*Primary Examiner*—Jacqueline V. Howard

(57) ABSTRACT

Specific substituted aromatic ester compounds are useful as lubricity additives for middle distillate fuel oils.

4 Claims, No Drawings

LUBRICITY ADDITIVES FOR FUEL OIL COMPOSITIONS

This application is a 371 of PCT /EP97/05105 Sep. 15, 1997

This invention relates to additives for improving the lubricity of fuel oils such as diesel fuel oil. Diesel fuel oil compositions including the additives of this invention exhibit improved lubricity and reduced engine wear.

Concern for the environment has resulted in moves to significantly reduce the noxious components in emissions when fuel oils are burnt, particularly in engines such as diesel engines. Attempts are being made, for example, to minimise sulphur dioxide emissions. As a consequence attempts are being made to minimise the sulphur content of fuel oils. For example, although typical diesel fuel oils have in the past contained 1% by weight or more of sulphur (expressed as elemental sulphur) it is now considered desirable to reduce the level to 0.2% by weight, preferably to 0.05% by weight and, advantageously, to less than 0.01% by weight, particularly less than 0.001% by weight.

Additional refining of fuel oils, necessary to achieve these low sulphur levels, often results in reductions in the level of polar components. In addition, refinery processes can reduce the level of polynuclear aromatic compounds present in such fuel oils.

Reducing the level of one or more of the sulphur, polynuclear aromatic or polar components of diesel fuel oil can reduce the ability of the oil to lubricate the injection system of the engine so that, for example, the fuel injection pump of the engine fails relatively early in the life of an engine. Failure may occur in fuel injection systems such as high pressure rotary distributors, in-line pumps and injectors. The problem of poor lubricity in diesel fuel oils is likely to be exacerbated by the future engine developments aimed at further reducing emissions, which will have more exacting lubricity requirements than present engines. For example, the advent of high pressure unit injectors is anticipated to increase the fuel oil lubricity requirement.

Similarly, poor lubricity can lead to wear problems in other mechanical devices dependent for lubrication on the natural lubricity of fuel oil.

Lubricity additives for fuel oils have been described in the art. WO 94/17160 describes an additive which comprises an ester of a carboxylic acid and an alcohol wherein the acid has from 2 to 50 carbon atoms and the alcohol has one or more carbon atoms. Glycerol monooleate is specifically disclosed as an example. Acids of the formula "$R^1$ (COOH)", wherein $R^1$ is an aromatic hydrocarbyl group are generically disclosed but not exemplified.

U.S. Pat. No. 3,273,981 discloses a lubricity additive being a mixture of A+B wherein A is a polybasic acid, or a polybasic acid ester made by reacting the acid with C1–C5 monohydric alcohols: while B is a partial ester of a polyhydric alcohol and a fatty acid, for example glycerol monooleate, sorbitan monooleate or pentaerythritol monooleate. The mixture finds application in jet fuels.

GB-A-1,505,302 describes ester combinations including, for example, glycerol monoesters and glycerol diesters as diesel fuel additives, the combinations being described as leading to advantages including less wear of the fuel-injection equipment, piston rings and cylinder liners. GB-A-1,505,302 is, however, concerned with overcoming the operational disadvantages of corrosion and wear by acidic combustion products, residues in the combustion chamber and in the exhaust system. The document states that these disadvantages are due to incomplete combustion under certain operating conditions. Typical diesel fuels available at the date of the document contained, for example, from 0.5 to 1% by weight of sulphur, as elemental sulphur, based on the weight of the fuel.

U.S. Pat. No. 3,287,273 describes lubricity additives which are reaction products of a dicarboxylic acid and an oil-insoluble glycol. The acid is typically predominantly a dimer of unsaturated fatty acids such as linoleic or oleic acid, although minor proportions of the monomer acid may also be present. Only alkane diols or oxa-alkane diols are specifically suggested as the glycol reactant.

U.S. Pat. No. 4,090,971 describes amides of substituted hydoxyaromatic carboxylic acids in which at least one substituent is a hydrocarbon-based radical containing at least about 10 carbon atoms, these materials being described as useful as dispersant additives. The amides can be prepared via reaction of an ester intermediate with the corresponding amine; vic-hydroxyalkyl esters of the acids are disclosed as suitable intermediates.

U.S. Pat. No. 5,089,158 describes derivatives of amides of an aromatic carboxylic acid having an ortho-hydroxy group in the form of a salt with a multivalent metal ion. The amide precursors for such materials may be prepared via an ester intermediate formed by the reaction of the requisite carboxylic acid and a C1 to C6 alkanol, this ester then being amidated by reaction with an amine.

U.S. Pat. No. 4,551,152 discloses that alcohol-containing fuels may exhibit poor corrosion and wear, caused by the presence of alcohol substances. This alcohol-related problem is said to be inhibited by the presence of an ester condensate. prepared from the reaction of a carboxy phenol with a polyol of the formula:

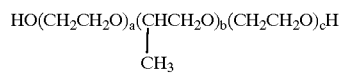

$$HO(CH_2CH_2O)_a(\underset{\underset{CH_3}{|}}{C}HCH_2O)_b(CH_2CH_2O)_cH$$

wherein a+c is 1–20 and b is 5–50, and subsequent reaction with an aldehyde and ethylene diamine to form the condensate product.

U.S. Pat. No. 5,462,567 discloses poly(oxyalkylene) hydroxyaromatic esters according to a certain formula, wherein the ester group links a polyoxyalkylene substituent containing at least 5 oxyalkylene units with the hydroxyaromatic ring. These compounds are described as deposit-controlling additives for, inter alia, diesel fuels, when used in combination with certain aliphatic amines.

U.S. Pat. No. 4,098,708 (filed in 1975 and published in 1978) describes esters of substituted hydroxyaromatic carboxylic acids in which at least one substituent is a hydrocarbon-based radical containing at least about 10 carbon atoms, with salicylic acid esters being preferred. The acids are reacted with mono- or polyhydric hydrocarbon-based alcohols such as glycerol, pentaerythritol and a variety of glycols. The esters are described as useful dispersant additives for lubricants and normally—liquid fuels, such as diesel fuel or fuel oil according to ASTM Specification D-395.

Such fuels typically contained much higher sulphur levels than those with which the present invention is concerned, as illustrated by the referenced ASTM Specification which recites, for 1975, maximum sulphur limits of as high as 0.5%. The corresponding ASTM Specification for diesel fuel (D-975) recites limits of between 0.5 and 2.0% sulphur, depending on the intended end use of the fuel.

There exists in the art a continual need for lubricity additives showing enhanced performance over existing materials, due not only to the development of engines with more exacting requirements, but also to the general demand from consumers and fuel producers for higher quality fuels.

In addition, there is a desire for additives to be handleable without the need for special operating measures. The extent to which an additive solidifies at lower ambient temperatures (e.g. via crystallisation) determines the extent to which an additive may be handled in the absence of heating and mixing procedures. Many conventional additives require substantial mixing and heating prior to addition to the fuel, and such operations can cause processing delays and may make the use of such additives uneconomic in spite of their performance-enhancing effects.

Furthermore, there is an increasing need in the art for 'multifunctional' additive compositions. Such compositions provide a range of performance-enhancing functions, typically through the incorporation therein of a number of individual additives each having its own function. The resulting complex mixtures often require addition to the fuel in relatively large amounts, and may also suffer from problems of physical and chemical interaction between individual additives which can impair their subsequent performance in the fuel. The provision of an individual additive with multiple performance-enhancing effects can reduce or avoid the need for such complex compositions and their associated problems.

It has now been found that certain esters of specific substituted aromatic carboxylic acids show improved lubricity performance over existing additives, particularly those of WO 94/17160. These materials can also display superior handleability. Some of these esters may also impart other performance-enhancing effects to fuel oils.

In a first aspect, this invention provides a fuel composition obtainable by the addition of a minor proportion of a compound comprising one or more aromatic ring systems wherein at least one of the ring systems bears, as substituents;

(i) one or more hydrocarbon groups imparting oil solubility to the compound, and (ii) one or more hydroxyl groups or derivatives thereof or both, and (iii) one or more ester groups of the formula

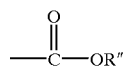

wherein R" represents an alkyl group optionally substituted by one or more heteroatom-containing groups to a major proportion of a liquid hydrocarbon middle distillate fuel oil having a sulphur concentration of 0.2% by weight or less, based on the weight of fuel.

In a second aspect, this invention provides a fuel oil composition obtainable by the addition, to the fuel oil defined under the first aspect, of an additive composition or concentrate into which has been incorporated the compound defined under the first aspect.

In a third aspect, this invention provides a compound comprising one or more aromatic ring systems, wherein at least one of the ring systems bears, as substituents;

(i) one or more hydrocarbon groups imparting oil solubility to the compound, and (ii) one or more hydroxyl derivatives of the formula —OR' wherein R' is hydrocarbyl or a group of the formula

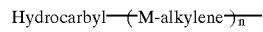

wherein M represents an oxygen atom or an NH group and n represents a number from 1 to 50, and (iii) one or more ester groups of the formula

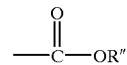

wherein R" represents an alkyl group optionally substituted by one or more heteroatom-containing groups.

Further aspects of this invention include an additive composition into which has been incorporated the compound of the third aspect, and an additive concentration obtainable by incorporating the compound or additive composition and optionally one or more additional additives, into a mutually-compatible solvent therefor.

The compounds defined under the first aspect of the invention provide, upon addition to low sulphur fuel oil, an improvement in fuel oil lubricity which can significantly exceed that obtainable from existing lubricity additives, and especially mixtures of the individual esters disclosed in WO 94/17160, even when such existing additives are used in substantially higher quantities (measured on an active-ingredient basis).

In particular, the specific compounds defined under the first and second aspects, and claimed under the third aspect, give higher lubricity performance even at treat rates as low as 15 to 50 parts per million by weight, per weight of fuel oil. Furthermore, some of these compounds may impart other performance-enhancing features to fuel oils, particularly detergency of engine fuel inlet systems and especially fuel injectors, reduced oxidation tendency especially during storage, and the ability to disperse insolubles which might otherwise give rise to harmful deposits and/or fuel line blockages. The detergency and dispersancy advantages may be apparent for those components wherein one or more of the substituents (ii) is a derivative of a hydroxyl group.

The Fuel Oil Composition of the First Aspect of the Invention

A The Compound

The compound may comprise one or more aromatic ring systems. By 'aromatic ring system' in this specification is mean a planar cyclic moiety which may be an aromatic homocyclic, heterocyclic or fused polycyclic assembly or a system where two or more such cyclic assemblies are joined to one another and in which the cyclic assemblies may be the same or different. It is preferred that the or each aromatic ring system is system based on heterocylic or homocyclic 5- or 6-membered rings, more preferably 6-membered rings and most preferably benzene rings.

The ring atoms in the aromatic system are preferably carbon atoms but may for example include one or more heteroatoms such as N, S, or O in the system in which case the compound is a heterocyclic compound.

Examples of suitable polycyclic assemblies include (a) condensed benzene structures such as naphthalene, anthracene, phenanthrene, and pyrene;

(b) condensed ring structures where none of or not all of the rings are benzene such as azulene, indene, hydroindene, fluorene, and diphenylene;

(c) rings joined "end-on" such as biphenyl; and (d) heterocyclic compounds such as quinoline, indole, 2:3 dihydroindole, benzofuran, benzothiophen, carbazole and thiodiphenylamine.

Where the compound comprises only one aromatic ring system, this system necessarily bears all three types of substituent (i), (ii) and (iii). It is preferred that one of each of the substituents (ii) and (iii) is present in such a compound. It is also preferred that one, two or three substituents (i) are present, at least one of which is capable of imparting oil solubility to the compound.

Where the compound comprises two or more aromatic ring systems, it is preferred that at least two, and preferably each, of the systems bears all three types of substituent (i), (ii) and (iii). It is preferred that each system bearing these three types of substituents bears one of each of substituent (ii) and (iii), and preferably one, two or three substituents (i), subject to the requirement that at least one of the substituents (i) provides oil solubility to the compound.

Particularly preferred are compounds wherein the or each aromatic ring system is a single, 6-membered ring, especially a benzene structure. Most preferably, the compound comprises a single benzene ring and one, two or three (preferably one or two) of the substituents (i) and having one of each of the (ii) and (iii) substituents, wherein substituent (ii) is a hydroxyl group.

Substituent (i) is a hydrocarbon group. By the term hydrocarbon as used in this specification in relation to substituent (i) is meant an organic moiety which is composed of hydrogen and carbon only, which is bonded to the rest of the molecule by a carbon atom or atoms which unless the context states otherwise, may be aliphatic, including alicyclic, aromatic or a combination thereof. It may be substituted or unsubstituted alkyl, aryl or alkaryl and may optionally contain unsaturation.

It is preferred that substituent (i) is aliphatic, for example alkyl or alkenyl, which may be branched or preferably straight-chain. Straight-chain alkyl is preferred.

It is essential for the good performance of the compound that at least one substituent of the formula (i) be a hydrocarbon group of sufficient oleophilic character to impart oil solubility to the compound. In this respect, it is preferred that at least one substituent (i) contains at least 8 carbon atoms, and preferably 10 to 200 carbon atoms. A substituent having 12 to 54, for example 14 to 36 carbon atoms is particularly preferred. Most preferred are alkyl or alkenyl groups containing 12 to 54 carbon atoms, especially straight chain alkyl groups. The groups having 14 to 20 carbon atoms are most advantageous.

Provided that the compound possesses at least one hydrocarbon substituent (i) imparting the requisite oil solubility, any additional substituents (i) may be of any character provided that they do not adversely interfere with the oil solubility of the compound.

Substituent (ii) is a hydroxyl group or derivative thereof, and can be represented by the formula —OR'. When a hydroxyl group, the compound may show particularly good performance as an oxidation inhibitor.

The hydroxyl group may be derivatised into a substituent capable of imparting other multifunctional character, for example a group of the form —OR' wherein R' is hydrocarbyl, or a linear or branched chain alkyleneoxyhydrocarbyl or poly(alkyleneoxy)hydrocarbyl group and/or a linear or branched chain alkyleneaminohydrocarbyl or (polyalkyleneamino)hydrocarbyl group having the formula:

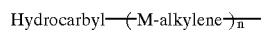

wherein M represents a oxygen atom or an NH group and n represents a number from 1 to 50, preferably 2 to 20, more preferably 2 to 10, for example 3 to 5. By the term hydrocarbyl in this specification is meant an organic moiety which is composed of hydrogen and carbon and which is bonded to the rest of the molecule by a carbon atom or atoms and which includes hydrocarbon groups as hereinbefore defined in relation to substituent (i), as well as predominantly-hdyrocarbon groups containing heteroatoms such as O, N or S provided that such heteroatoms are insufficient to alter the essentially hydrocarbon nature of the group. The hydrocarbyl group in substituent (ii) may especially be substituted, preferably terminally substituted, by a heteroatom-containing group, for example a hydroxyl or amino group. Small hydrocarbyl groups, such as those containing 1 to 24, preferably 1 to 18, for example 2 to 12, are particularly advantageous. The alkylene group may contain 1 to 6, for example 2 to 4 methylene units and may also optionally be substituted by such a heteroatom containing group or groups. R' may be bonded directly to the oxygen depending from the ring system or indirectly via a linking group, such as a carbonyl group. The heteroatom-containing derivatives of the hydroxyl group, useful as substituent (ii), may be particularly beneficial in providing dispersant and/or detergent properties when used in fuel oils. Postulated in this respect are derivatives of the formula —O(CH$_2$)$_{n'}$—NH$_2$ wherein n' represents a number from 1 to 24, preferably 1 to 18, more preferably 2 to 6.

Substituent (iii) is an ester group, wherein the carbonyl carbon of the ester is bonded indirectly, or preferably directly, to a ring atom of the aromatic ring system and more preferably to a ring carbon. The ester group is of the formula:

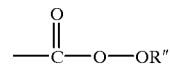

wherein the group —OR" is derivable from the corresponding alcohol HOR", wherein R" represents an alkyl, preferably n-alkyl group, and especially one having 1 to 30, preferably 1 to 22, carbon atoms and optionally substituted by one or more heteroatom-containing groups, such as hydroxyl groups.

Particularly good results have been achieved when the alcohol HOR" is a mono or polyhydroxy alcanol, each hydroxyl group being bonded to a different carbon atom of the alcanol. Examples of suitable monohydroxy alcohols include C1 to C20 alkanols, for example methanol, ethanol, proponol, butanol and 2-ethyl hexanol. C1 to C10, for example C1 to C8, alkanols are preferred, the resulting ester group in the compound thus comprising an alkyl substituent.

The most favoured alcohols are polyhydroxyalcanols giving rise in the compound to ester groups comprising hydroxy-substituted alkyl substituents. Suitable polyhydroxy alcanols are aliphatic, saturated or unsaturated, straight chain or branched alcohols having 2 to 10, preferably 2 to 6, more preferably 2 to 4, hydroxyl groups, and having 2 to 90, preferably 2 to 30, more preferably 2 to 12, most preferably 2 to 5, carbon atoms in the molecule. As examples, the polyhydroxy alcohol may be a glycol or diol, or a trihydroxy alcohol. Ethylene glycol and glycerol are most highly preferred. Compounds comprising one or more substituents (iii) derived from such polyhydroxy alcanols have been found to exhibit particularly good lubricity activity at low treat rates.

In the compound, the substituents (ii) and (iii) are preferably positioned vicinally on the aromatic ring system from which they depend. Where the system is polycyclic they are preferably positioned vicinally on the same ring of the polycyclic system, for example in an ortho position to each other, although they may be positioned on different rings. The or each substituent (i) may be positioned vicinally to any of the substituents (ii) or (iii), or in a position further removed in the ring system.

The compound may also be of oligomeric structure, such as a series of aromatic ring systems connected via esterification with polyhydric alcohols, or via alkylene bridges produced, for example, by the phenol-formaldehyde type condensation reaction of several aromatic ring systems with an aldehyde. Particularly useful are methylene-bridged compounds wherein each aromatic ring system is preferably a homocyclic, six-membered ring and wherein, more preferably, each ring carries at least one of each of the substituents (i), (ii) and (iii).

A preferred form of the compound can be represented by the following general formula: (I)

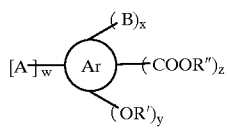

wherein Ar represents an aromatic ring system, —B, —OR' and —COOR" represent substituents (i), (ii) and (iii) respectively as hereinbefore defined, and A represents a group of the formula (II):

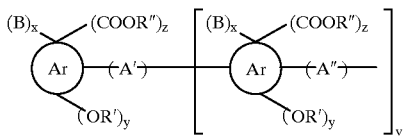

wherein Ar, B, R' and R" are as hereinbefore defined in formula (I) and A' and A" each independently represent hydrocarbylene groups; and wherein:

v represents an integer in the range of from 0 to 10;

w represents an integer in the range of from 0 to 3;

and x, y and z each independently represent an integer in the range of from 1 to 3.

Preferably, R' represents hydrogen, or a hydrocarbyl group, or a poly(alkyleneoxy)alkyl or poly(alkyleneamino) alkyl group optionally substituted by one or more heteroatom-containing groups, and wherein R' may be bonded either directly to the oxygen depending from the ring system, or indirectly via a linking group; and R" preferably represents a hydrocarbyl group optionally substituted by one or more heteroatom-containing groups, or a poly (alkyleneoxy)alkyl or poly(alkyleneamino)alkyl group, also optionally so substituted.

Preferably, x represents 1 or 2, especially when y and z each represent 1. When w is 1 to 3, v is preferably 1 to 9, for example 2 to 5, such as 3. Alternatively, v maybe 0 (zero). A' and A" are preferably methylene or substituted methylene groups.

When w=o, the compound comprises a single aromatic ring system having substituents (i), (ii) and (iii). It is preferred that when w=o, y and z each=1 and x=1 or 2; more preferably, R" represents an alkyl or hydroxylalkyl group and R' represents hydrogen. Most preferably, Ar represents a benzene ring; w=0; x=1 or 2; y and z each=1; R" represents a hydroxylalkyl group and R' represents hydrogen.

Most preferably, the compound is the ethylene glycol or glycerol ester of alkyl-substituted salicylic acid, the alkyl substituent or substituents of the acid containing between 14 and 18 carbon atoms.

The mechanism of action of the compound is not clearly understood. However, it is postulated that the specific substituted aromatic ring system or systems form a flat region within the molecule, the or each hydroxyl or hydroxyl-derivatised group and ester group contributing to an electronic and polar character across this flat region which is surprisingly effective at surface adsorption and improving the fuels' ability to lubricate critical metal surfaces in the injection system, and particularly in the injection pump. Heteroatom substituents on the ester group are also believed to contribute to additive performance.

The compound may be prepared by conventional means. Thus, for example, the compound may be prepared by esterification of a precursor compound having the requisite aromatic ring system or systems bearing substituent(s) (i), substituent(s) (ii) and one or more carboxylic acid substituents, or acylating derivatives thereof, capable of esterification with compounds having at least one hydroxyl group to form substituent (iii).

The esterification reaction is preferably performed in the presence of an acidic or basic catalyst. Suitable acidic catalysts include sulphuric acid, paratoluene sulphonic acid or a macroreticular resin like amberlyst with sulphonic acid groups. Suitable basic catalysts include organotitanates, e.g. titanium tetrabutoxide, organo zirconates or sodium methoxide.

Alternatively, and particularly when using polyhydroxy-alcohols such as ethylene glycol or glycerol, the esterification reaction may be performed via a two-stage transesterification process. The acid is first esterified with a simple, low boiling alcohol like methanol or butanol, and then transesterified using the desired polyhydroxyalcohol under base catalysis, the low boiling alcohol being continuously removed by distillation to drive the reaction.

A further alternative route for the formation of useful β-hydroxy esters is via a ring opening reaction of the reactant carboxylic acid compound with an epoxide, using a basic catalyst such as lithium hydroxide or carbonate. This route is particularly suitable for the formation of ester groups equivalent to those derived from the reaction of the acid group with alcohols having hydroxy groups at both the 1-carbon and 2-carbon positions, such as 1,2-dihydroxyethane (ethylene glycol) or glycerol. Suitable epoxides include 1,2-epoxyethane and 1,2-epoxypropane, glicydol (2,3-epoxypropan-1-ol) or difunctional compounds such as the diglicydyl ether of ethylene glycol.

The precursor compound may itself be prepared by hydrocarbylation of a suitable hydroxyl-substituted aromatic ring system compound, for example by an electrophilic substitution reaction using a halide derivative of the desired hydrocarbyl substituent(s), for example via a Friedel-Crafts type reaction using iron (iii) chloride as catalyst. Alternatively, hydrocarbylation can be achieved through reaction of the corresponding alkene using a hydrogen fluoride and boron trifluoride catalyst system, or hydrogen chloride and aluminium trichloride catalyst system. The resulting hydrocarbyl-substituted, hydroxyl-substituted aromatic compound may be carboxylated, for example via the 'Kolbe-Schmitt' reaction comprising the reaction of a salt, preferably an alkali metal salt, of the hydrocarbyl substituted, hydroxyl-substituted aromatic compound with carbon dioxide and subsequently acidifying the salt thus obtained. Alternatively, a Friedel-Crafts acylation-type reaction product may be used to add the required carboxylic acid substituent(s). This acid may be derivatised into an acylating group such as an acid halide group, for example an acid chloride group, order to facilitate the subsequent esterification reaction. The above types of reaction are well-known in the chemical art.

The preferred precursor compounds are carboxylic acid derivatives of hydrocarbyl-substituted phenols and/or napthols, with phenols being the most preferred. Particularly preferred are the hydrocarbyl-substituted salicylic acids, which typically comprise a mixture of mono and disubstituted acids. These materials are readily available in a form suitable for the esterification reaction, without the need for further modification.

During the esterfication reaction, incomplete conversion to the ester product(s) may result, especially when the precursor compound is a carboxylic acid rather than an acylating derivative thereof. The degree of esterification can be monitored during the reaction, for example by total acid number (TAN-ASTM D-974/95).

It is preferred that the degree of esterification is at least 10%, preferably at least 30%, and more preferably at least 30%, by weight of the original amount of acid or derivative reactant acid. Good results have been obtained in the range of 70–90% esterification.

B The Middle Distillate Fuel Oil

The fuel oil has a sulphur concentration of 0.2% by weight or less based on the weight of the fuel, and preferably 0.05% or less, more preferably 0.03% or less, such as 0.01% or less, most preferably 0.005% or less and especially 0.001% or less. Such fuels may be made by means and methods known in the fuel-producing art, such as solvent extraction, hydrodesulphurisation and sulphuric acid treatment.

As used in this specification, the term "middle distillate fuel oil" includes a petroleum oil obtained in refining crude oil as the fraction between the lighter kerosene and jet fuels fraction and the heavier fuel oil fraction. Such distillate fuel oils generally boil within the range of about 100° C., eg 150° to about 400° C. and include those having a relatively high 95% distillation point of above 360° C. (measured by ASTM-D86). In addition, "city-diesel" type fuels, having lower final boiling points of 260–330° C. and particularly also sulphur contents of less than 200 ppm (and preferably 50 ppm and particularly 100 ppm (wt/wt)) are included within the term 'middle distillate fuel oil'.

Middle distillates contain a spread of hydrocarbons boiling over a temperature range, including n-alkanes which precipitate as wax as the fuel cools They may be characterised by the temperatures at which various %'s of fuel have vaporised ('distillation profile'), e.g. 50%, 90%, 95%, being the interim temperatures at which a certain volume % of initial fuel has distilled. They are also characterised by pour, cloud and CFPP points. as well as their initial boiling point (IBP) and 95% distillation point or final boiling point (FBP). The fuel oil can comprise atmospheric distillate or vacuum distillate, or cracked gas oil or a blend in any proportion of straight run and thermally and/or catalytically cracked distillates. The most common middle distillate petroleum fuel oils are diesel fuels and heating oils. The diesel fuel or heating oil may be a straight atmospheric distillate, or it may contain minor amounts, e.g. up to 35 wt %, of vacuum gas oil or cracked gas oils or of both.

Heating oils may be made of a blend of virgin distillate, eg gas oil, naphtha, etc and cracked distillates, eg catalytic cycle stock. A representative specification for a diesel fuel includes a minimum flash point of 38° C. and a 90% distillation point between 282 and 380° C. (see ASTM Designations D-396 and D-975).

As used in this specification, the term 'middle distillate fuel oil' also extends to biofuels, or mixtures of biofuels with middle distillate petroleum fuel oils.

Biofuels, ie fuels from animal or vegetable sources are believed to be less damaging to the environment on combustion, and are obtained from a renewable source. Certain derivatives of vegetable oil, for example rapeseed oil, eg those obtained by saponification and re-esterification with a monohydric alcohol, may be used as a substitute for diesel fuel. It has recently been reported that mixtures of biofuels, for example, between 5:95 and 10:90 by volume are likely to be commercially available in the near future.

Thus, a biofuel is a vegetable or animal oil or both or a derivative thereof.

Vegetable oils are mainly triglerides of monocarboxylic acids, eg acids containing 10–25 carbon atoms and of the following formula:

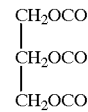

wherein R is an aliphatic radical of 10–25 carbon atoms which may be saturated or unsaturated.

Generally, such oils contain glycerides of a number of acids, the number and kind varying with the source vegetable of the oil.

Examples of oils are rapeseed oil, coriander oil, soyabean oil, cottonseed oil, sunflower oil, castor oil, olive oil, peanut oil, maize oil, almond oil, palm kernel oil, coconut oil, mustard seed oil, beef tallow and fish oils. Rapeseed oil, which is a mixture of fatty acids particularly esterified with glycerol, is preferred as it is available in large quantities and can be obtained in a simple way by pressing from rapeseed.

Examples of derivatives thereof are alkyl esters, such as methyl esters, of fatty acids of the vegetable or animal oils. Such esters can be made by transesterification.

As lower alkyl esters of fatty acids, consideration may be given to the following, for example as commercial mixtures: the ethyl, propyl, butyl and especially methyl esters of fatty acids with 12 to 22 carbon atoms, for example of lauric acid, myristic acid, palmitic acid, palmitoleic acid, stearic acid, oleic acid, petroselic acid, ricinoleic acid, elaeostearic acid, linoleic acid, linolenic acid, eicosanoic acid, gadoleic acid, docosanoic acid or erucic acid, which have an iodine number from 50 to 150, especially 90 to 125. Mixtures with particularly advantageous properties are those which contain mainly, ie. to at least 50 wt % methyl esters of fatty acids with 16 to 22 carbon atoms and 1, 2 or 3 double bonds. The preferred lower alkyl esters of fatty acids are the methyl esters of oleic acid, linoleic acid, linolenic acid and erucic acid.

Commercial mixtures of the stated kind are obtained for example by cleavage and esterification of natural fats and oils by their transesterification with lower aliphatic alcohols. For production of lower alkyl esters of fatty acids it is advantageous to start from fats and oils with high iodine number, such as, for example, sunflower oil, rapeseed oil, coriander oil, castor oil, soyabean oil, cottonseed oil, peanut oil or beef tallow. Lower alkyl esters of fatty acids based on a new variety of rapeseed oil, the fatty acid component of which is derived to more that 80 wt % from unsaturated fatty acids with 18 carbon atoms, are preferred.

The above described biofuels may be used in blends with middle distillate petroleum fuel oils. Such blends typically contain 0 to 10% by weight of the biofuel and 90 to 100% by weight of the petroleum fuel oil, although other relative proportions may also be used to advantageous effect. Particularly useful are blends of biofuels with 'city-diesel' type fuel oils which exhibit extremely low levels of sulphur and are therefore particularly prone to lubricity problems.

In the fuel oil composition of the sixth aspect, the concentration of the compound incorporated into the oil may for example be in the range of 0.5 to 1,000 ppm of additive (active ingredient) by weight per weight of fuel, for example 1 to 500 ppm such as 10 to 200 ppm by weight per weight of fuel, preferably 10 to 100 ppm, more preferably 15 to 50 ppm.

In addition to middle distillate fuel oils, other fuels having a need for increased lubricity, such as fuels (e.g. future gasoline) intended for high pressure fuel injection equipment, may suitably be treated with the additives of the invention.

The Fuel Oil Composition of the Second Aspect of the Invention

C The Additive Composition

The additive composition defined under the second aspect is prepared by the incorporation of the compound into a composition itself comprising one or more additives for fuel oils. Such incorporation may be achieved by blending or mixing, either with an existing composition or with the components thereof, to produce the additive composition of the first aspect of the invention. However, the term 'incorporation' within the meaning of this specification extends not only to the physical mixing of the compound with other materials, but also to any physical and/or chemical interaction which may result upon introduction of the compound, or upon standing.

Many fuel oil additives are known in the art and may be used to form the composition into which the compound is incorporated. Such additives include for example the following; detergents, antioxidants, corrosion inhibitors dehazers, demulsifiers, metal deactivators, antifoaming agents, cetane improvers, combustion improvers, dyes, package compatibilisers, further lubricity additives and antistatic additives. Cold flow-improving additives may also be present.

D The Additive Concentrate Composition

The concentrate may be obtained by incorporating the compound or the additive composition into a mutually-compatible solvent therefor. The resulting mixture may be either a solution or a dispersion, but is preferably a solution. Suitable solvents include organic solvents including hydrocarbon solvents, for example petroleum fractions such as naphtha, kerosene, diesel and heating oil; aromatic hydrocarbons such as aromatic fractions, eg. those sold under the 'SOLVESSO' tradename; and paraffinic hydrocarbons such as hexane and pentane and isoparaffins.

Further solvents include oligomers and hydrogenated oligomers of alkenes such as hydrogenated decene-1 dimer or trimer. Also useful are alcohols and esters especially higher alcohols such as liquid alkanols having at least eight carbon atoms. An especially useful solvent is isodecanol. Mixtures of such solvents maybe used in order to produce a mutually-compatible solvent system.

The concentrate may contain up to 80% by weight, for example 50% of solvent.

The concentrate is particularly convenient as a means for incorporating the additive composition of the first aspect into fuel oil where despite the presence of the compound, the co-presence of other additives in the composition demands an amount of solvent in order to impart handleability. However, concentrates comprising the compound as sole additive may also be used, especially where small quantities of additives are required and the equipment present for introduction of the additive lacks the necessary accuracy to measure or handle such small volumes.

As indicated above, the compound defined under the first aspect, and the additive composition and concentrate defined under the second aspect, find application in low sulphur fuel oils.

A further aspect of this invention is therefore the use of the compound, or the additive composition or concentrate, in a liquid hydrocarbon middle distillate fuel oil, having a sulphur concentration of 0.2% by weight or less, per weight of fuel, particularly to improve the lubricity thereof. This invention also provides a method for improving the lubricity of a liquid hydrocarbon middle distillate fuel oil having a sulphur concentration of 0.2% by weight based on the weight of fuel, comprising the addition thereto of the additive composition or concentrate, or of the compound.

Where the fuel oil composition is produced by incorporation of the additive or concentrate composition, the amount used of each of these compositions will be such as to ensure the incorporation to the fuel oil of the requisite amount of the compound. For example, however, the amount of additive or concentrate composition will usually be in the range of 1 to 5,000 ppm (active ingredient) by weight per weight of fuel, especially 10 to 2000 ppm such as 50 to 500 ppm.

The Compound of the Third Aspect

The compound claimed under the third aspect comprises one or more hydroxyl derivatives of the formula —OR' wherein R' is as defined in relation to the first aspect but is not hydrogen. Such materials may show good performance as lubricity improvers and as detergents and/or dispersants in low sulphur middle distillate fuel oils.

The invention will now be described further by reference to the examples only as follows:

EXAMPLE 1

Preparation of the Compounds

Compounds as defined under the first aspect of the invention were prepared via esterification of hydrocarbyl-substituted salicylic acid compounds with 1,2-dihydroxy ethane (ethylene glycol). The synthetic procedures used are given below.

In each case, the hydrocarbyl substituents on the salicylic acid were n-alkyl groups ranging in carbon number from 14 to 18 and predominately C18 alkyl. Most of the salicylic acid reactant was mono alkylated although a proportion was dialkylated with two such alkyl groups.

Ester A

In a 5-necked round bottom flask equipped with a mechanical stirrer, a nitrogen sparge and a Dean-Stark condenser were placed 100 g of alkylsalicylic acid (65% Al in xylene, total acid number of 87.2 mg KOH/g), 32.6 gms of 1,2-dihydroxyethane, 100 g of toluene and 1.5 g of paratoluenesulphonic acid. The mixture was heated at reflux temperature for 6 hours and then transferred to a rotary evaporator. The product was dried at 130° C. under vacuum. The TAN of the final product was 88.4 mg KOH/g corresponding to 33% conversion of the acid to ester product.

Ester B

The procedure for ester A was repeated except that the toluene was replaced by the same amount of solvent 30 (an aliphatic solvent). The TAN of the final product was 86.7 mg KOH/g corresponding to 35% conversion of the acid to ester product.

The reaction products of these syntheses thus showed, by TAN, incomplete esterification ie. some unreacted acid remained in the end product.

A further esterification product was obtained by the transesterification of the methyl ester of the substituted salicylic acid used for esters A and B by 1,2-dihydroxyethane, as described below.

Ester C (i) Preparation of the methyl ester of alkyl salicylic acid

In a 5 necked round bottom flask equipped with a mechanical stirrer, a nitrogen sparge and a Dean-Stark condenser were placed 329 g of alkylsalicylic acid (65% Al in xylene), 349 g of methanol and 16.7 g of 90% sulfuric acid. The mixture was refluxed at 65–66° C. for 16.5 hours.

The mixture was concentrated by boiling off 322 ml of methanol leading to a phase separation of the mixture. The reaction mixture was decanted into a separating funnel and the bottom layer, approximately 40 ml consisting of xylene and sulfuric acid, was removed. The top layer was washed 5 times with 100 ml of distilled water and finally dried in a rotary evaporator at 118° C. to give 203 g of material with a TAN of 81.3 mg KOH/g.

(ii) Transesterification reaction

In the same 5 necked flash were placed 75 g of the previously prepared methyl ester, 145 g of 1,2-dihydroxyethane and, 232 g of solvent 30 and 2 g of paratoluenesulfonic acid. The mixture was heated under reflux at 107° C. for 10 hours. The volatile solvents and unreacted material were then removed using a rotary evaporator at 130° C. to give 81 g of material with a TAN of 72.7 mg KOH/g corresponding to a 45% conversion of the acid to ester product.

A fourth esterification product was prepared by an epoxide ring-opening reaction using glycidol (1-hydroxy-2, 3-epoxypropane).

Ester D

To a 3 necked flask was added 100 g of the alkylsalicylic acid (TAN of 129 mg KOH/g), 100 g of toluene and 0.058 g of lithium hydroxide monohydrate. The mixture was heated at 105° C. whilst glycidol (16 g ) was added dropwise with a dropping funnel over a 4.5 hours period. The mixture was then stripped in a rotary evaporator at 90° C. The final material has a TAN of 26.4 mg KOH/g corresponding to 80.4% conversion of the acid to ester product.

EXAMPLE 2

Lubricity Performance

Esters A, B, C and D were added to a low sulphur middle distillate fuel oil having the following characteristics:

| | |
|---|---|
| Density @ 15° C. | 0.8256 |
| Cloud Point, ° C. (CP) | −11 |
| WAT ° C. | −14.62 |
| % Wax @ 5° C. below CP | 1.58 |
| % Wax @ 10° C. below CP | 2.78 |
| Sulphur, ppm, w/w | 210.9 |
| HFRR @ 60° C. (wear scar diameter) | 548 $\mu$m |
| D86 Distillation | |
| IBP | 157 |
| 5% | 186 |
| 10% | 194 |
| 20% | 208 |
| 30% | 222 |
| 40% | 237 |
| 50% | 251 |
| 60% | 266 |
| 70% | 280 |
| 80% | 296 |
| 90% | 315 |
| 95% | 328 |
| FBP | 345 |
| FBP-90% | 30 |
| 90%–20% | 107 |

The resulting fuel oil compositions were tested in the High Frequency Reciprocating Rig Test (or "HFRR") for lubricity performance and compared to a sample of the fuel oil treated with salicylic acid (Comparative No 1), and a sample treated with an ester mixture prepared by esterification of a commercial mixture of oleic and linoleic acids with glycerol (Comparative No 2). The mixed ester product of Comparative No. 2 predominated in (a) glycerol monooleate and (b) glycerol monolinoleate, in approximately equal proportions by weight, with minor amounts of glycerol di- and trioleate and linoleate also present. In addition, the commercial acid mixture used to make this comparative additive contained a minor proportion of other acids, the esters of which were not believed to represent more than about 6% by weight of the mixed ester product. The HFRR test method is described in the industry standard test methods CEC PF 06-T-94 and ISO/TC22/SC7/WG6/W188 and was performed at 60° C.

The amounts of each additive used and the results of the HFRR tests are shown in Table 1.

TABLE 1

| Additive Treat Rate (ppm active Ingredient w/w) | HFRR Wear Scar Diameter (μm) at 60° C. | | | | | |
|---|---|---|---|---|---|---|
| | Comparative No. 1 | Ester A | Ester B | Ester C | Ester D | Comparative No. 2 |
| 0 | 548 | 548 | 548 | 548 | 548 | 548 |
| 7.3 | | 506 | | | | |
| 7.6 | | | 562 | | | |
| 9.9 | | | | 503 | | |
| 13.8 | | | | 387 | | |
| 14.6 | | 353 | | | | |
| 15.2 | | | 380 | | | |
| 17.6 | | | | | 336 | |
| 19.8 | | | | 331 | | |
| 21.5 | 541 | | | | | |
| 24.7 | | | | | 333 | |
| 25.0 | | | | | | 494 |
| 29.2 | | 355 | | | | |
| 30.4 | | | 340 | | | |
| 35.3 | | | | | 276 | |
| 42.9 | 533 | | | | | |
| 50.0 | | | | | | 414 |
| 58.4 | | 355 | | | | |
| 60.8 | | | 394 | | | |
| 79.0 | | | | 335 | | |
| 85.8 | 395 | | | | | |
| 100.0 | | | | | | 252 |
| 141.0 | | | | | | |
| 171.6 | 350 | | | | 346 | |

In the Table, no entry at a particular treat rate means no measurement was made at that treat rate for that additive.

The active ingredient levels tested for each additive varied slightly due to the differences in conversion obtained in each synthesis.

In conclusion, it can be seen that compositions comprising the compound defined under the first aspect of the invention were surprisingly more potent as lubricity additives in comparison to other esters.

EXAMPLE 3

Handleability

The handleability of esters A and C as prepared above were compared with that of the reactant alkylsalicylic acid and with a commercial lubricity additive comprising a mixture of oleic and linoleic acid esters of glycerol (Comparative No. 2 from Example 2).

In each case, the material was stored at −10° C. in both undiluted and diluted form and the appearance and behaviour noted after 42 days, simulating field storage during a substantial period of cold weather. The results are shown in Table 2.

TABLE 2

| Additive | % wt Aromatic Solvent (diluent) | Appearance/Behaviour after 42 days @ −10° C. |
|---|---|---|
| Ester A | 0 | Homogeneous-mobile liquid |
| | 30 | Homogeneous-mobile liquid |
| | 50 | Homogeneous-mobile liquid |
| Ester C | 0 | A few crystals formed |
| | 30 | Homogeneous-mobile liquid |
| | 50 | Homogeneous-mobile liquid |
| C$_{14-18}$ Alkylsalicylic Acid | 0 | Phase separation |
| | 30 | Crystals formed |
| | 50 | Hazy mixture |

TABLE 2-continued

| Additive | % wt Aromatic Solvent (diluent) | Appearance/Behaviour after 42 days @ −10° C. |
|---|---|---|
| Commercial Glycerol Esters Mixture | 0 | Solid |
| | 30 | Phase separation |
| | 50 | A few crystals formed |

The esters A and C thus showed significantly better cold temperature storage properties, both in diluted and undiluted form, indicating better handleability in the absence of heating and mixing equipment.

What is claimed is:

1. A fuel oil composition obtainable by the addition, to a major proportion of a liquid hydrocarbon middle distillate fuel oil having a sulfur concentration of 0.2% by weight of less, based on the weight of fuel, of a minor proportion of either (a) a compound of the general formula (I):

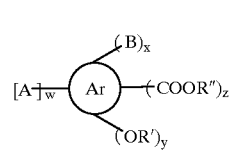

(I)

wherein Ar represents an aromatic ring system;
B represents a hydrocarbon group (i);
OR' represents a hydroxyl group or derivative thereof (ii) wherein R' represents hydrogen, or a hydrocarbyl group, or a group of the formula

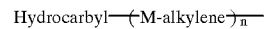

wherein M represents an oxygen atom or an NH group and n represents a number from 1 to 50, and wherein R' may be bonded either directly to the oxygen depending from the ring system or indirectly via a linking group;

—COOR" represents an ester group (iii) wherein R" represents an alkyl group optionally substituted by one or more hydroxyl groups, and A represents a group of the formula (II):

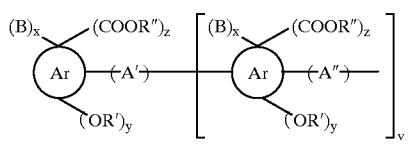

(II)

wherein Ar, B, R' and R" are as defined above, and A' and A" each independently represent hydrocarbylene groups, and wherein v represents an integer in the range of from 0 to 10, w represents an integer in the range of from 1 to 3, and x, y and z each independently represent an integer in the range of from 1 to 3;

(b) an additive composition comprising one or more additives for fuel oils and into which has been incorporated the compound (a); or (c) an additive concentrate obtainable by incorporating the compound (a) or additive composition (b), and optionally one or more additional additives, into a mutually-compatible solvent therefor.

2. The composition of claim 1 wherein each aromatic ring system of the compound is a single, six-membered ring.

3. The composition of claim 1 wherein the ester group comprises an alkyl or hydroxy-substituted alkyl substituent.

4. A method for improving the lubricity of a liquid hydrocarbon middle distillate fuel oil having a sulphur concentration of 0.2% by weight or by less based on the weight of fuel, comprising the addition thereto of the compound 15–50 ppm of or additive composition or concentrate defined in claim 1.

* * * * *